United States Patent

Gusakov et al.

[11] Patent Number: 5,803,639
[45] Date of Patent: Sep. 8, 1998

[54] APPARATUS FOR REMOVING MEDICAL ADHESIVE DEVICES FROM SKIN

[75] Inventors: Ignaty Gusakov, Aurora; George T. Bauer, Williamsville, both of N.Y.

[73] Assignee: Graphic Controls Corporation, Buffalo, N.Y.

[21] Appl. No.: 626,056

[22] Filed: Apr. 1, 1996

[51] Int. Cl.⁶ ..................................................... A61B 19/00
[52] U.S. Cl. ............................................................. 401/139
[58] Field of Search ...................................... 401/137, 138, 401/139

[56] References Cited

U.S. PATENT DOCUMENTS

| | | |
|---|---|---|
| D. 338,298 | 8/1993 | Grim, Sr. . |
| 1,268,271 | 6/1918 | Nelson . |
| 1,598,811 | 9/1926 | Ferrin . |
| 1,738,471 | 12/1929 | D'Amore . |
| 1,789,959 | 1/1931 | Fedeler ................. 401/139 X |
| 1,861,790 | 5/1932 | Schultheiss . |
| 1,982,833 | 12/1934 | Schmerler . |
| 2,014,149 | 9/1935 | Stafford ................. 401/139 |
| 2,104,161 | 1/1938 | Koukal . |
| 2,321,333 | 6/1943 | Terry . |
| 2,584,735 | 2/1952 | Pancoast . |
| 2,804,767 | 9/1957 | Schoen . |
| 2,832,980 | 5/1958 | O'Neill . |
| 2,943,338 | 7/1960 | Lowen ................. 401/139 X |
| 3,041,655 | 7/1962 | Entler . |
| 3,081,481 | 3/1963 | Nohl et al. ................. 401/138 |
| 3,108,313 | 10/1963 | Summers et al. . |
| 3,351,969 | 11/1967 | Cline . |
| 3,534,428 | 10/1970 | Pugh et al . |
| 3,749,502 | 7/1973 | Kreihe ................. 401/139 |
| 3,782,600 | 1/1974 | Columbus ................. 401/139 X |
| 3,998,654 | 12/1976 | Falaas et al. . |
| 4,662,768 | 5/1987 | Gottwald et al. . |
| 4,750,883 | 6/1988 | Drake . |
| 4,812,070 | 3/1989 | Marty . |
| 4,867,981 | 9/1989 | Grof . |
| 5,007,753 | 4/1991 | England, Jr. . |
| 5,106,221 | 4/1992 | Diot et al. . |
| 5,189,756 | 3/1993 | Sprunger . |
| 5,312,197 | 5/1994 | Abramson ................. 401/139 X |
| 5,316,403 | 5/1994 | Mansour . |
| 5,415,488 | 5/1995 | MacGibbon et al. . |
| 5,433,782 | 7/1995 | Filbert et al. ................. 401/139 X |

FOREIGN PATENT DOCUMENTS

| | | | |
|---|---|---|---|
| 2662145 | 11/1991 | France | ................. 401/139 |
| 8506654 U | 6/1985 | Germany . | |

OTHER PUBLICATIONS

Aerospace Material Specification AMS 1320A by The Engineering Society for Advancing Mobility Land Sea Air & Space, Jul. 15, 1978, pp. 1–5.

Barbara B. Weber and Kathleen S. Stone, "Application & Removal of Adhesive Tapes: Does It Make a Difference in Skin Repair?", Focus on Critical Care, Jun. 1988, vol. 15, No.3, pp. 50–53.

Chemicals and Components, "Adhesive Remover," Adhesives Age, Apr. 1993, p.10.

J.A. Fries et al., "Pressure Sensitive Adhesives for Medical Applications," National Starch and Chemical Corporation Specialty Adhesives, 1984. TAPPI. Reprinted from Proceedings of the Technical Assn. of the Pulp & Paper Industry, 1984 Polymers, Laminations & Coatings Conference, pp. 479–483, with permission.

European Search Report dated Oct. 15, 1997.

*Primary Examiner*—William E. Stoll
*Attorney, Agent, or Firm*—Ratner & Prestia

[57] ABSTRACT

A scraping apparatus or scraper for contacting an adhesive device and skin to which the adhesive device is attached, at an interface between the adhesive device and the skin, to remove the adhesive device from the skin. In one configuration, the scraping apparatus includes a fluid for reducing the adhesion of the adhesive; an element for holding the fluid; and a scraping component. The scraping component is connected to and in fluid communication with the fluid holding element and has at least one first opening distal to the fluid holding element. The scraping apparatus also includes a structure for closing the first opening. In another configuration, the scraping apparatus further includes an element for propelling the fluid to the scraping component. The propelling element may be a compressed gas.

40 Claims, 8 Drawing Sheets

5,803,639

APPARATUS FOR REMOVING MEDICAL ADHESIVE DEVICES FROM SKIN

FIELD OF THE INVENTION

This invention relates generally to an apparatus for removing adhesive devices from skin and, more particularly, to an apparatus for removing adhesive medical devices.

BACKGROUND OF THE INVENTION

The removal of medical adhesive devices such as electrocardiograph electrodes, electrosurgical grounding pads, transdermal drug patches and medical tapes from the skin has long been a source of discomfort and pain for patients. Electrocardiograph electrodes, for example, are adhered to the patient's skin with strong pressure sensitive adhesives that aid in providing stable electrical contact between the electrode and the skin. To achieve adequate contact between the adhesive device and the skin, the skin often must be shaved, further adding to the patient's discomfort. In the event the skin is not shaved the removal of the adhesive device usually tears the hair from the skin and causes the patient severe pain.

The previous methods and devices used to remove adhesive medical devices from skin include contacting the adhesive device with a solvent, for example, on a gauze pad to dissolve the adhesive and then pulling the adhesive device from the skin. Alternatively, the adhesive device simply may be pulled from the skin without pretreating the adhesive device with a solvent. For permeable or semi-permeable adhesive devices, such as some medical tapes, contacting the adhesive device with a solvent sufficiently dissolves the adhesive and satisfactorily reduces the discomfort to the patient during removal. For impermeable adhesive devices, however, it is difficult or impossible to contact the adhesive sufficiently with solvent through the adhesive device. A new scraping apparatus is provided to overcome these shortcomings.

It is an object of the present invention to provide an easy to use and inexpensive, disposable or reusable scraping apparatus to painlessly and quickly remove adhesive medical devices from the skin, to eliminate the need to shave the area on which the adhesive device is placed, to prevent hair from being torn out of the patient's skin, and to increase comfort for the patient during attachment (by omitting the necessity to shave the patient) and removal of the adhesive device.

SUMMARY OF THE INVENTION

To achieve these and other objects, and in view of its purposes, the present invention provides a simple to use, inexpensive, disposable or reusable scraping apparatus (or scraper) which allows the painless and fast removal of medical adhesive devices from a patient's skin to which the adhesive device is attached. The apparatus contacts the interface between the adhesive device and the skin. The apparatus includes, in one configuration, a fluid for reducing or eliminating the adhesion of the adhesive on the adhesive device; an element for holding the fluid; and a scraping component connected to and in fluid communication with the fluid holding element. The scraping apparatus has at least one first opening distal to the fluid holding element and a closure for that first opening. Preferably, the scraping apparatus has more than one first opening at or around the scraping tip of the scraping component to allow the fluid to be dispensed therethrough.

In another configuration, the fluid holding element is adjacent to the scraping component, and the scraping apparatus further includes an element for propelling the fluid to the scraping component. The propelling element is adjacent to and in fluid communication with the fluid holding element and the scraping component. The propelling element may be a compressed gas.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawings in which.

DETAILED DESCRIPTION OF THE INVENTION

Figure 1A:
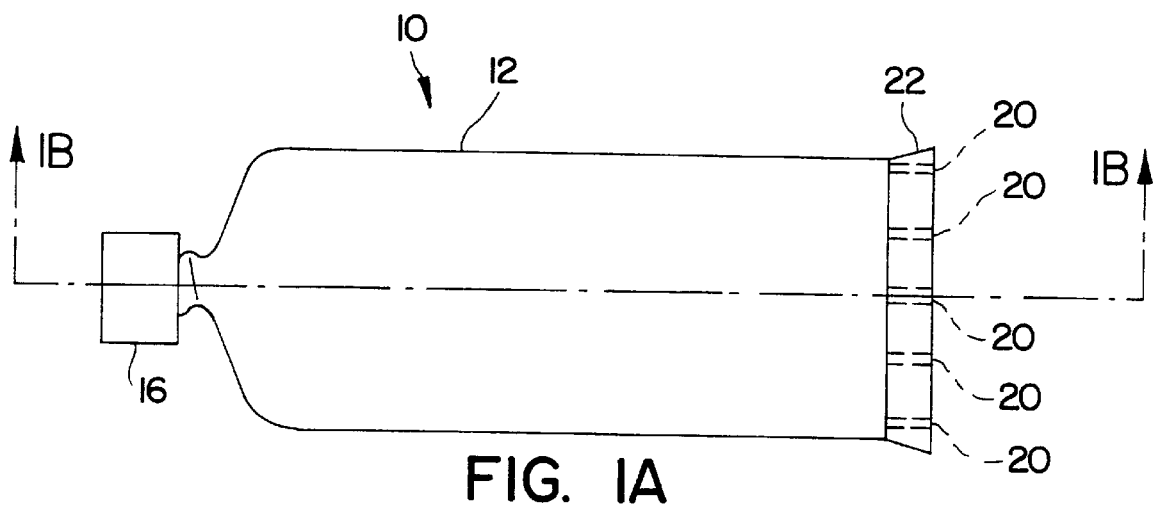
FIG. 1A is a top view of one embodiment of the scraping apparatus according to the present invention.
Figure 1B:
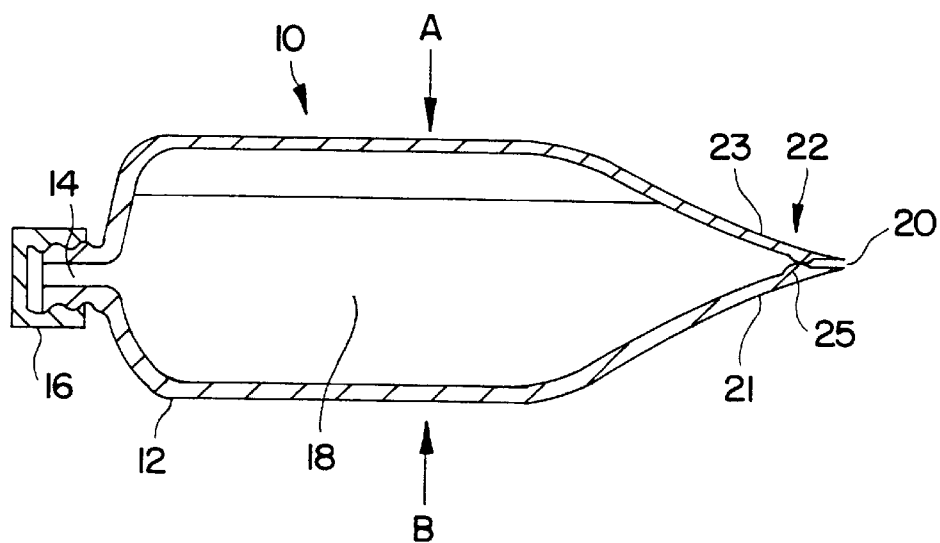
FIG. 1B is a sectional side view of the scraping apparatus shown in FIG. 1A taken along line 1B—1B.

Referring now to the drawing, wherein like reference numerals refer to like elements throughout, FIGS. 1A–1B show a scraping apparatus or scraper 10 according to a first embodiment of the invention. A tubular housing 12 of scraper 10 has an opening 14 at one end which receives, for example, a hollow, threaded cap 16, and a tapered end 22 at the other end. Opening 14 allows a fluid 18 to be introduced into housing 12 and may be annular in shape. Tapered end 22 has two opposing faces 21 and 23. Cap 16 mates with opening 14 and can be removed to fill scraper 10 with fluid 18. Optionally, cap 16 is a constrictive device such as a clamp or a pincher (not shown). Also, opening 14 may be sealed by heat sealing, an adhesive, or the like. In tapered end 22, at least one hole or passage 20 allows, and preferably a plurality of holes or passages 20 allow, fluid 18 to flow from housing 12 and to be dispensed at the interface 26 between skin 24 of a patient and an adhesive device 28 (as shown in FIG. 1C).

Figure 1C:
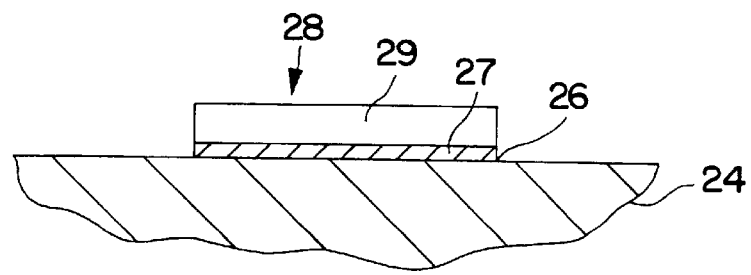
FIG. 1C is a sectional side view of an adhesive device attached to the skin of a patient.

FIG. 1C shows an adhesive device 28 attached to skin 24. Adhesive device 28 may be, for example, a pressure sensitive, adhesive-backed electrocardiograph electrode attached to skin 24, an electrosurgical grounding pad (not shown), or a transdermal drug delivery patch (not shown). Adhesive device 28 includes adhesive 27 and foam backing 29. Fluid 18 is any gas or liquid capable of reducing or eliminating the adhesion of adhesive 27 on adhesive device 28. Fluid 18 may be a liquid or gas solvent or solvent-like material; a heated or cooled liquid or gas; or the like. A solvent or solvent-like material as used herein is any gas or liquid that will reduce or eliminate the adhesion of adhesive 27. For example, the liquid solvent or solvent-like material is an alcohol such as propyl alcohol, isopropyl alcohol (rubbing alcohol), or the like. In addition, a gaseous solvent or solvent-like material may be used. The heated or cooled liquid or gas is, for example, an inert gas, an inert liquid, air or water. Fluid 18 may further include a small amount of an oil or detergent so that fluid 18 may be used on patients with particularly sensitive skin. A closure 25 prevents fluid 18 from escaping from scraper 10 and is held in a closed position by a spring force produced by faces 21 and 23 biased against one another at tapered end 22. Tapered end 22 and closure 25 are formed, for example, by thermoforming or compressing the material which forms housing 12. Optionally, other means may be used to prevent fluid 18 from escaping from scraper 10. For example, a wick (not shown in FIGS. 1A–1B, but see FIG. 2B) formed of an absorbent material may be disposed in the tip of scraper 10.

In use, as a clinician compresses tubular housing 12 in the direction of arrows "A" and "B" in FIG. 1B, fluid pressure builds up within housing 12. Then, the compression forces acting on opposing faces 21 and 23 of closure 25, and fluid pressure building within housing 12, cause closure 25 to open and release a volume of fluid 18 through passage 20 sufficient to reduce or eliminate the adhesion of adhesive 27. In this way fluid 18 contacts and reduces the adhesion of adhesive 27, for example by dissolving adhesive 27 on adhesive device 28, and allowing adhesive device 28 to be painlessly removed from skin 24. When the clinician stops compressing tubular housing 12 in the direction of arrows "A" and "B," opposing faces 21 and 23 are released and biased against one another to form closure 25. When used on hairy skin, the thin matted hair forms channels through which fluid 18 can flow by capillary action. Housing 12 is formed of a semi-rigid material such as polyvinyl chloride (PVC), polyethylene, polypropylene, metal such as aluminum foil, or the like that will retain its shape after compression. Housing 12 may be formed of two pieces of material which are connected together by heat sealing, gluing, or the like. Optionally, housing 12 may be integrally formed by thermoforming, blow molding, extrusion, or injection molding and is similar to formed tubular containers used for toothpaste, gels and many other products in common usage.

Figure 2A:
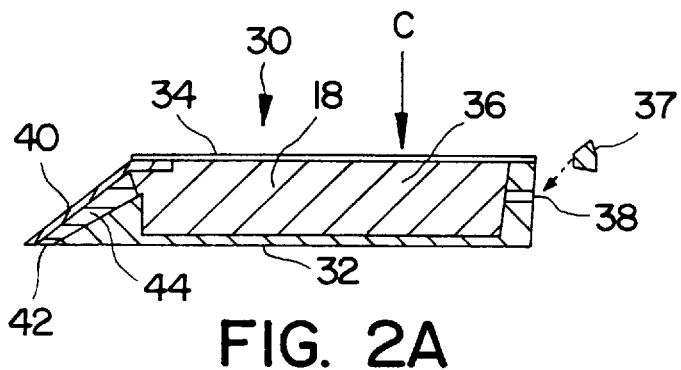
FIG. 2A is a sectional side view of a second embodiment of the scraping apparatus according to the invention taken along line 2A—2A in FIG. 2B.
Figure 2B:
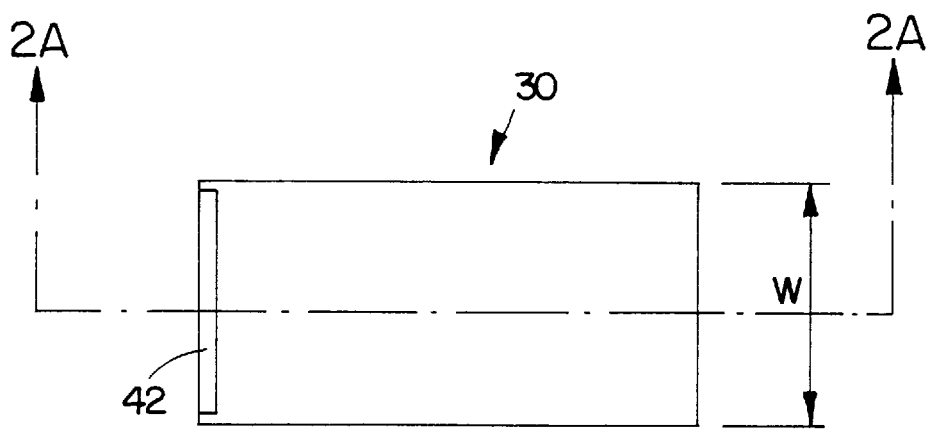
FIG. 2B is a bottom view of the scraping apparatus shown in FIG. 2A.

FIGS. 2A and 2B show a second embodiment of the present invention. Scraper 30 has a width "W" which is somewhat larger than the width of the adhesive device 28 to be removed. For example, scraper 30 is preferably about one-quarter to one-half inch wider than the width of the adhesive device 28 to be removed. Scraper 30 includes a rigid or semi-rigid housing 32 and a thin, flexible sheet or membrane 34. A cavity 36 formed in housing 32 is filled with fluid 18 through an aperture 38 which receives a plug 37 after filling. A sloping wall 40 of housing 32 provides scraper 30 with a wedge-like or blade-like surface which aids in removing adhesive device 28. Housing 32, flexible sheet or membrane 34, and sloping wall 40 are cemented together, for example, with an adhesive that cannot be dissolved by fluid 18. Optionally, these components may be assembled using ultrasonic welding, heat sealing or other fastening means. These components also may be integrally formed. A dispenser 42 which may be a narrow slit (as shown in FIGS. 2A, 2B, 4A, 4B, and 5) or a plurality of holes (as shown in FIGS. 6A and 6B) is or are provided in housing 32.

Figure 3:
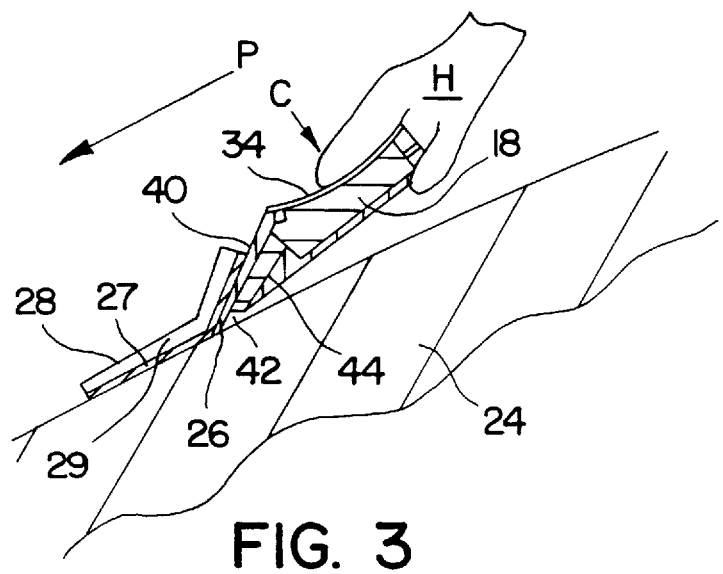
FIG. 3 is a sectional side view of the scraping apparatus shown in FIGS. 2A and 2B being used to remove an adhesive device from the skin.

In use, when flexible sheet or membrane 34 is pressed downward in the direction of arrow "C," typically by hand "H" of a clinician, fluid 18 is forced through dispenser 42 as shown in FIG. 3. Then, forced by the downward pressure on flexible sheet or membrane 34, fluid 18 is applied to interface 26 between skin 24 and adhesive device 28 to reduce or eliminate the adhesion of adhesive 27. The user simultaneously pushes scraper 30 with a sweeping or scraping motion along skin 24 (in the direction of arrow "P") to peel adhesive device 28 from skin 24. In most cases the removal of adhesive device 28 from skin 24 can be accomplished with one hand. In special cases, however, as when removing adhesive devices from especially sensitive areas such as a woman's breast, it might be necessary to help remove adhesive device 28 by lifting the edge of adhesive device 28 with one hand while operating scraper 30 with the other. A wick 44 retains fluid 18 in scraper 30 until scraper 30 is used to remove adhesive device 28 from skin 24. In the embodiments shown in FIGS. 2A, 2B, 3, 6A, and 6B, dispenser 42 is on the bottom of scraper 30. In the embodiments shown in FIGS. 4A, 4B, and 5, however, dispenser 42 may be formed at one location or more than one location at the end of scraper 30 as discussed below.

Figure 4A:
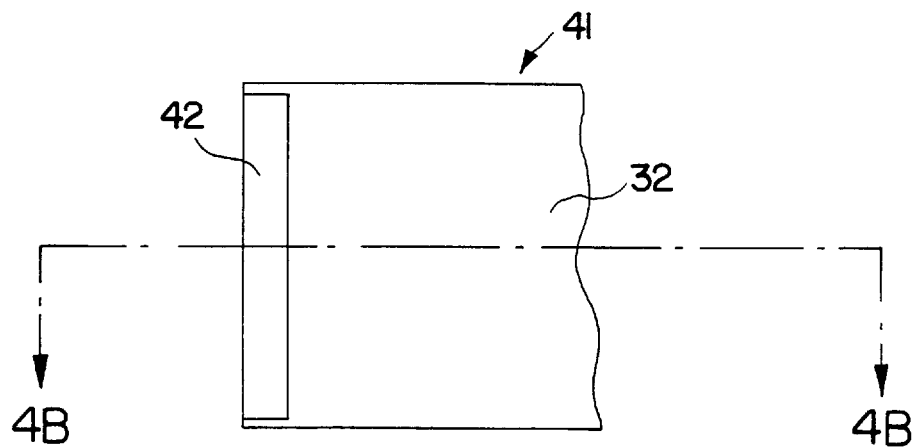
FIG. 4A is a partial top view of a third embodiment of the scraping apparatus according to the present invention.
Figure 4B:
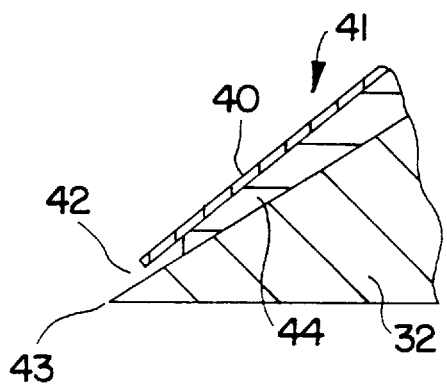
FIG. 4B is a partial sectional side view of the scraping apparatus shown in FIG. 4A taken along line 4B—4B.

FIGS. 4A and 4B show a third embodiment of the present invention which is a variation of the embodiment shown in FIGS. 2A and 2B. In this embodiment, scraper 41 has sloping wall 40 which does not extend to meet the tip of housing 32, leaving a gap which forms dispenser 42 in sloping wall 40. By disposing dispenser 42 above housing 32, fluid 18 is applied to adhesive 27 above skin 24 at the interface of adhesive 27 and foam backing 29. In use, fluid 18 initially reduces or eliminates the adhesion of adhesive 27, for example by dissolving adhesive 27, in the direction from foam backing 29 to skin 24 to loosen the adhesion of adhesive device 28 on skin 24. A tip 43 of housing 32 lifts the front edge of adhesive device 28 to initiate removal of adhesive device 28 from skin 24 and allows fluid 18 to contact adhesive 27 at the intersection of adhesive 27 and skin 24.

Figure 5:
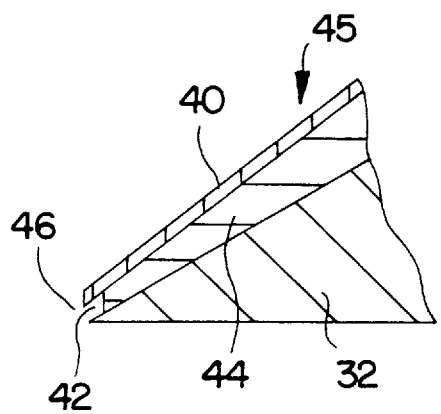
FIG. 5 is a partial sectional side view of a fourth embodiment of the scraping apparatus according to the present invention.
Figure 6A:
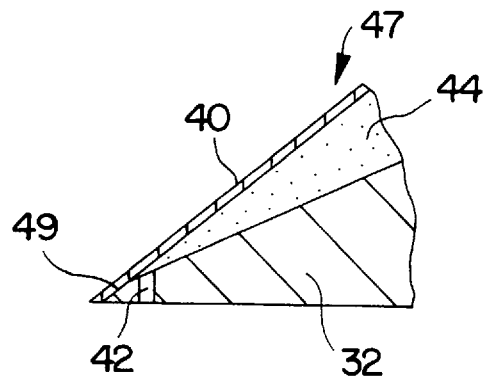
FIG. 6A is a partial sectional side view of a fifth embodiment of the scraping apparatus according to the present invention.
Figure 6B:
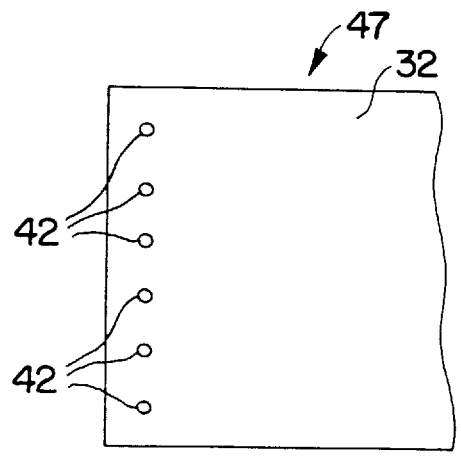
FIG. 6B is a partial bottom view of the scraping apparatus shown in FIG. 6A.

FIG. 5 shows a fourth embodiment of the present invention which is another variation of the embodiment shown in FIGS. 2A and 2B. In this embodiment, scraper 45 has dispenser 42 disposed at an apex 46 formed by sloping wall 40 and housing 32. In use, fluid 18 is dispensed from dispenser 42 and contacts adhesive 27 at the interface of adhesive 27 and skin 24 to reduce or eliminate the adhesion of adhesive 27, for example, by dissolving the layer of adhesive 27 in contact with skin 24. Then, the adhesion of adhesive 27 is progressively reduced or eliminated in the direction from the skin 24 to foam backing 29. The adhesion of adhesive 27 to skin 24 is reduced first at the interface of skin 24 and adhesive 27 allowing quick removal of adhesive device 28. Further, because dispenser 42 is not covered by a layer of adhesive 27 on adhesive device 28, as scraper 45 removes adhesive device 28, the chance of clogging dispenser 42 with adhesive 27 is reduced.

FIGS. 6A and 6B show a fifth embodiment of the present invention. In this embodiment, scraper 47 has dispenser 42 which is at least one hole, and preferably a plurality of holes, disposed in the bottom of housing 32. In use, the intersection 49 of housing 32 and sloping wall 40 first lifts the front edge of adhesive device 28 from skin 24 while fluid 18 is dispensed through the dispenser 42. Fluid 18 then flows along the surface of skin 24 to contact the interface 26 between skin 24 and adhesive 27 on adhesive device 28. By disposing dispenser 42 on the bottom of housing 32, dispenser 42 will not become clogged with adhesive 27. Alternatively, dispenser 42 can be in both sloping wall 40 and housing 32 as discussed below with respect to FIGS. 13–16. This configuration allows fluid 18 to be dispensed through sloping wall 40 and housing 32 at the same time.

Figure 7A:
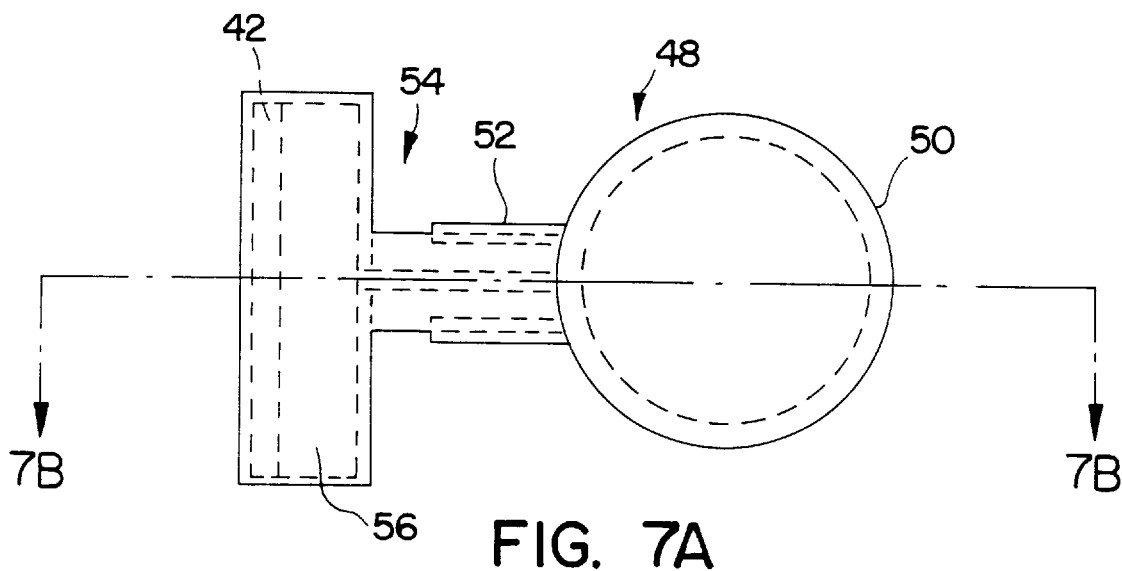
FIG. 7A is a top view of a sixth embodiment of the scraping apparatus according to the present invention.
Figure 7B:
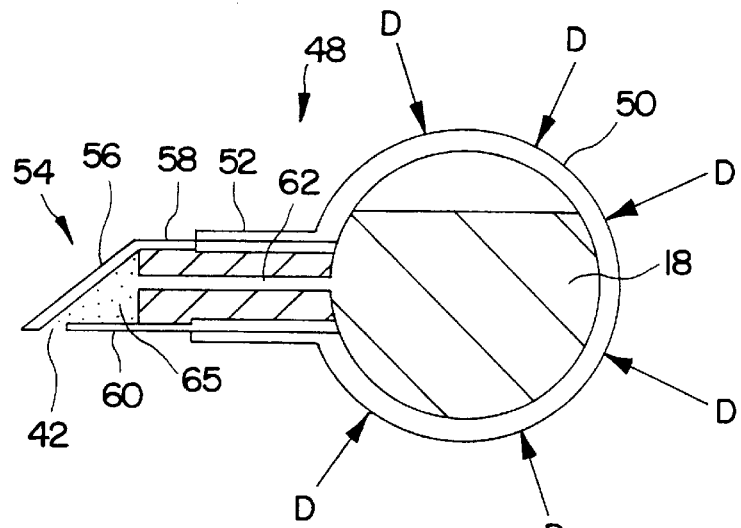
FIG. 7B is a side sectional view of the scraping apparatus shown in FIG. 7A taken along line 7B—7B.

FIGS. 7A and 7B show a sixth embodiment of the present invention. In this embodiment, scraper 48 includes a reservoir 50 having tubular opening 52. Reservoir 50 is, for example, ball-shaped, cube-shaped, rectangular-shaped or regular- or irregular-shaped. Reservoir 50 is formed, for example, from a flexible material such as silicone rubber. Scraper 48 further includes a T-shaped distributor 54 having a sloping wall 56, a top wall 58, a bottom wall 60, and a dispenser 42. Sloping wall 56, top wall 58, and bottom wall 60 are assembled using an adhesive that cannot be dissolved by fluid 18. Optionally, these components may be assembled using heat sealing or may be integrally formed. The T-shaped distributor 54 slideably fits into tubular opening 52 and dispenser 42 is in fluid communication via an annular opening 62 with reservoir 50. Optionally, the T-shaped distributor 54 and reservoir 50 may have corresponding threads allowing the two components to be screwed together. Dispenser 42 may be a narrow slit or a plurality of holes. By squeezing reservoir 50 at its circumference along lines "D," fluid 18 is forced through dispenser 42 to contact interface 26 of adhesive device 28 and skin 24 to which adhesive device 28 is attached as discussed with respect to the above-described embodiments. Wick 65 retains fluid 18 in scraper 48 until reservoir 50 is squeezed.

Figure 8:
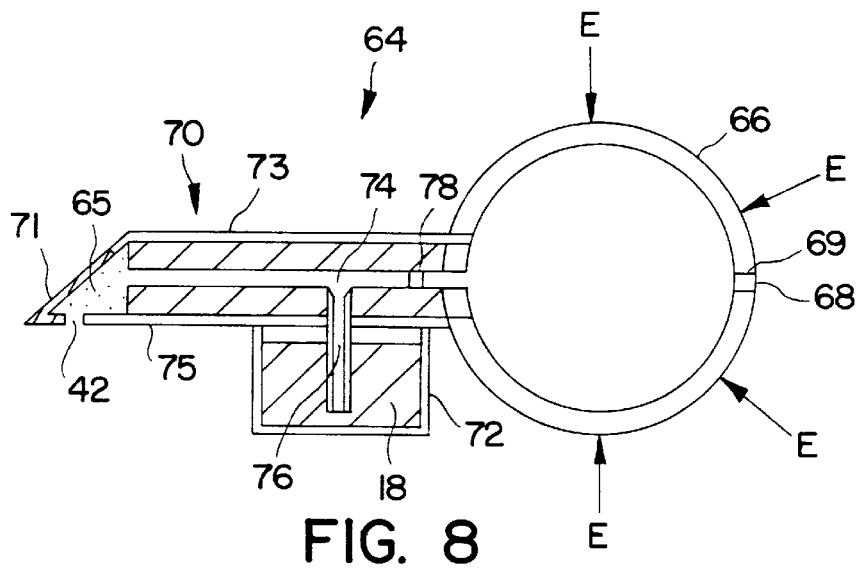
FIG. 8 is a sectional side view of a seventh embodiment of the scraping apparatus according to the present invention.

FIG. 8 shows a seventh embodiment of the present invention. In this embodiment, scraper 64 includes reservoir 66 having an air passage 68 holding a check valve 69. For example, reservoir 66 is ball-shaped, cube-shaped, rectangular-shaped, or regular- or irregular-shaped. Check valve 69 prevents the air contained within reservoir 66 from escaping through air passage 68 when reservoir 66 is compressed along lines "E." Then, as reservoir 66 is allowed to expand, check valve 69 allows air to be sucked into reservoir 66 through air passage 68. Scraper 64 further includes a T-shaped distributor 70 having a sloping wall 71, a top wall 73, a bottom wall 75, and a dispenser 42. Dispenser 42 may be a narrow slit or a plurality of holes. The T-shaped distributor 70 has a fluid reservoir 72 holding fluid 18. Fluid reservoir 72 is in fluid communication with first annular opening 74 via second annular opening 76. First annular opening 74 has check valve 78 disposed therein between second annular opening 76 and reservoir 66. Check valve 78 allows one-way flow of air in the direction of sloping wall 71 when reservoir 66 is compressed along lines "E." Check valve 78 also prevents fluid 18 from entering reservoir 66 when the clinician stops compressing reservoir 66 along lines "E." Sloping wall 71, top wall 73, bottom wall 75, and fluid reservoir 72 are assembled using an adhesive that can not be dissolved by fluid 18. Optionally, those components may be assembled using heat sealing or may be integrally formed.

In use, as reservoir 66 is compressed at its circumference along lines "E," check valve 69 closes and check valve 78 opens forcing air at great speed through check valve 78 and, by reducing the pressure (Bernoulli's equation) in first annular opening 74, the forced air siphons and atomizes fluid 18 from fluid reservoir 72. Atomized fluid 18 exits T-shaped distributor 70 through dispenser 42 to contact interface 26 of adhesive device 28 and skin 24 to which adhesive device 28 is attached as discussed with respect to the above-described embodiments.

Figure 9A:
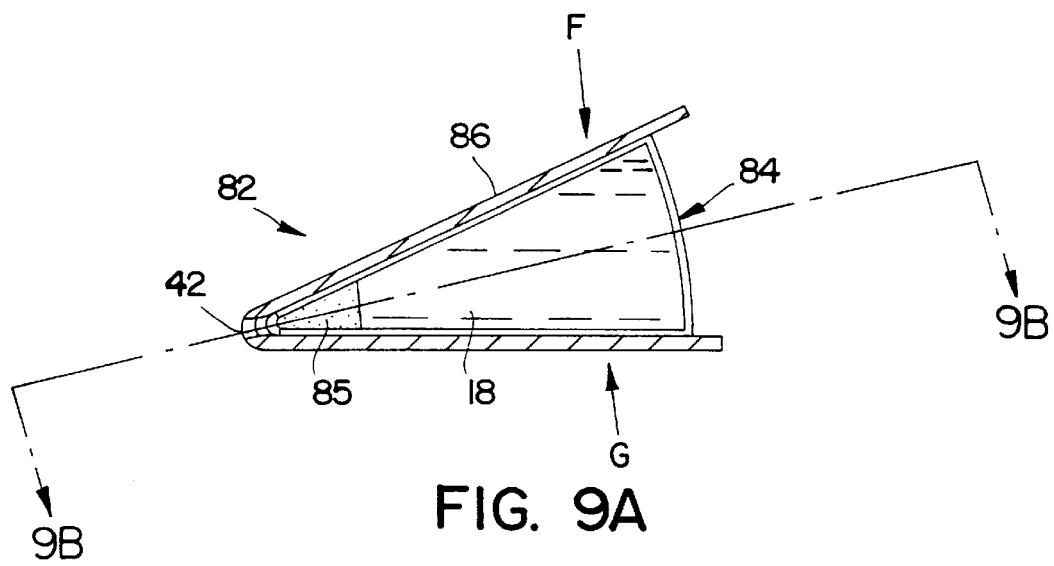
FIG. 9A is a sectional side view of an eighth embodiment of the scraping apparatus according to the present invention.
Figure 9B:
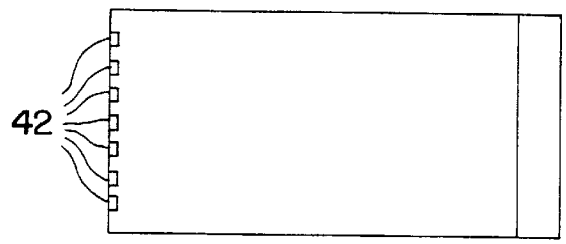
FIG. 9B is a sectional top view of the scraping apparatus shown in FIG. 9A taken along line 9B—9B.

FIGS. 9A and 9B show an eighth embodiment of the present invention. Scraper 82 comprises flexible reservoir 84 which is formed, for example, of silicone rubber or thin aluminum. Flexible reservoir 84 is placed in V-shaped housing 86 which is formed, for example, of PVC, polyethylene, polypropylene, or the like. Flexible reservoir 84 and V-shaped housing 86 include dispenser 42 which may be a plurality of holes or a narrow slit. Wick 85 retains fluid 18 in scraper 82 until it is used. In use, V-shaped housing 86 is compressed along lines "F" and "G" to force fluid 18 through dispenser 42. At the same time, the tip of V-shaped housing 86 and fluid 18 contact interface 26 of adhesive device 28 and skin 24 to which adhesive device 28 is attached to remove adhesive device 28 as discussed with respect to the above-described embodiments.

Figure 10:
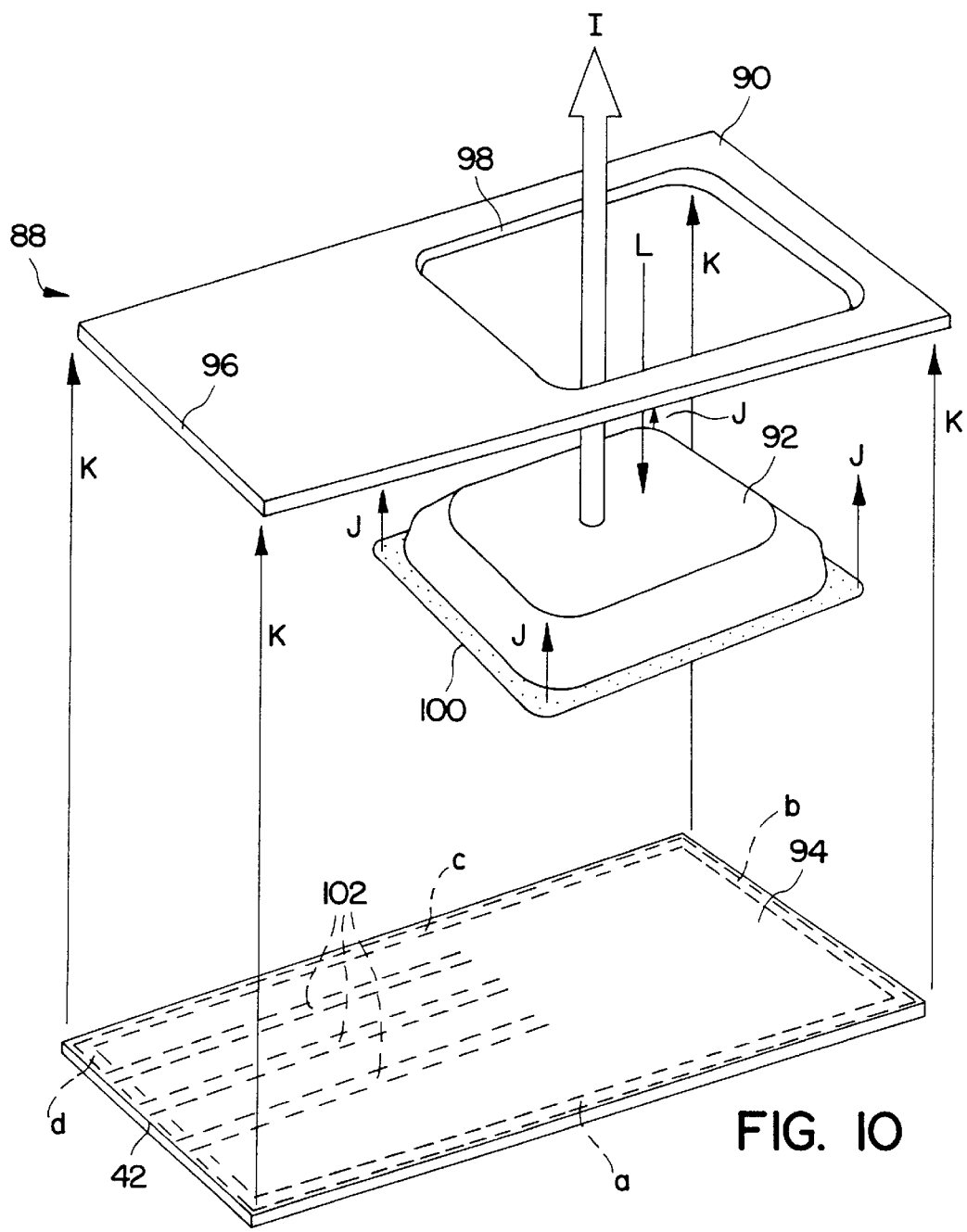
FIG. 10 is an exploded perspective view of a ninth embodiment of the scraping apparatus according to the present invention.

FIG. 10 shows a ninth embodiment of the present invention. Scraper 88 includes top plate 90, fluid container 92, and bottom plate 94. Top plate 90 is formed of a rigid or semi-rigid plastic and has beveled edge 96 which aids to remove adhesive device 28 from skin 24, and cut-out 98 in which fluid container 92 is disposed. The fluid container 92 is a flexible, thermoformed, squeezable container and has flat edge 100. Fluid container 92 is heat sealed or glued with adhesive along all four edges to top plate 90. The arrows marked "I" and "J" indicate the direction in which fluid container 92 is inserted into cut-out 98 of top plate 90. Top plate 90 and bottom plate 94 are assembled along the arrows marked "K" and are heat sealed or glued together with adhesive along three edges marked "a", "b", and "c" of bottom plate 94 leaving an opening at one end forming dispenser 42.

Bottom plate 94 is formed of a rigid or semi-rigid plastic and, optionally, includes at least one formed groove or channel 102, and preferably a plurality of formed grooves or channels 102, extending from dispenser 42 to fluid container 92. Fluid container 92 is in fluid communication with dispenser 42 providing flow of fluid 18 along top plate 90 and bottom plate 94. Where groove or channel 102 is, or grooves or channels 102 are, present, bottom plate 96 may be glued or heat sealed along edge "d" thereof in the areas surrounding the groove(s) or channel(s). In this way, when bottom plate 94 is attached to top plate 90, the groove or channel 102 serves, or grooves or channels 102 serve, as flow paths for fluid 18 to reach dispenser 42.

In use, as fluid container 92 is depressed in the direction of arrow "L," fluid pressure builds up in fluid container 92, forcing fluid 18 to flow between top and bottom plates 90 and 94 to dispenser 42. Fluid 18 then contacts interface 26 of adhesive device 28 and skin 24 to which adhesive device 28 is attached to reduce or eliminate the adhesion of adhesive 27 as discussed with respect to the above-described embodiments. Then, as fluid container 92 is depressed, scraper 88 is moved in a motion parallel, perpendicular or both with respect to interface 26 of adhesive device 28 and skin 24 to remove adhesive device 28 from skin 24.

Figure 11A:
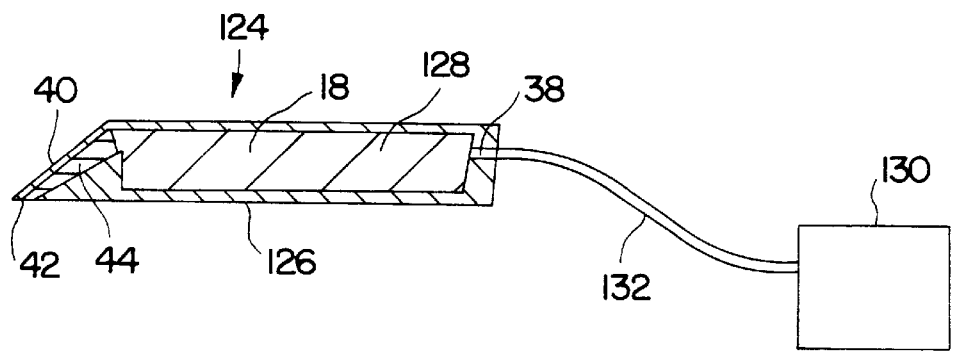
FIG. 11A is a sectional side view of a tenth embodiment of the scraping apparatus according to the invention taken along line 11A—11A in FIG. 11B.
Figure 11B:
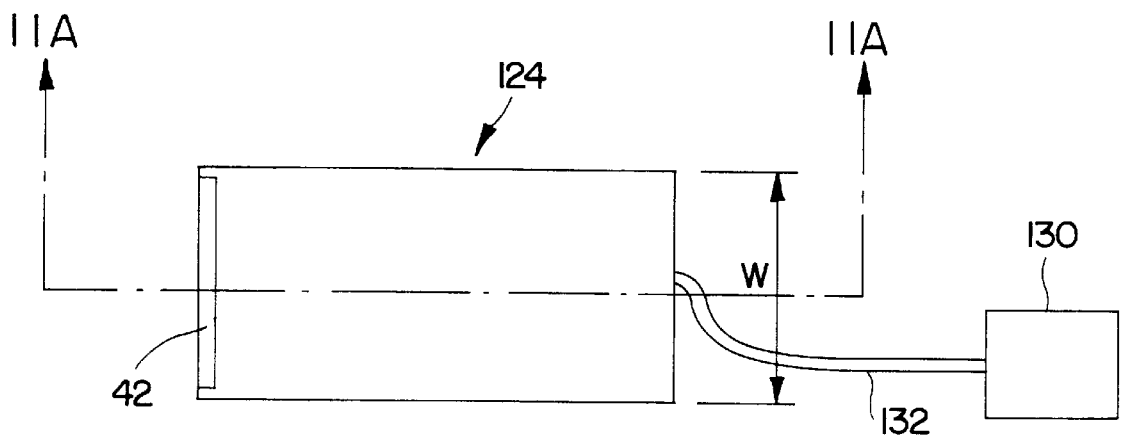
FIG. 11B is a bottom view of the scraping apparatus shown in FIG. 11A.

FIGS. 11A and 11B show a tenth embodiment of the present invention which is a variation of the second embodiment shown in FIGS. 2A and 2B. This embodiment further includes, however, an external source of a compressed gas such as inert gas or air, or any heated or cooled gas, or the like, which will not deteriorate the adhesion-reducing characteristics of fluid 18 and is suitable for medical use. In this embodiment, scraper 124 includes a rigid housing 126 enclosing a cavity 128 which is filled with fluid 18. A sloping wall 40 of housing 126 provides scraper 124 with a wedge-like or blade-like surface which aids in removing adhesive device 28 attached to skin 24 of a patient. Housing 126 and sloping wall 40 are cemented together with an adhesive having adhesion strength which will not be reduced by fluid 18. Alternatively, these components can be heat sealed or may be integrally formed. A dispenser 42, which may be a narrow slit or a plurality of holes, is provided in an end of housing 126. Scraper 124 further includes a source of compressed gas 130 such as an inert gas or air. Compressed gas source 130 may be, for example, an air pump or a compressor which is attached via conduit 132 to aperture 38 in housing 126. Conduit 132 is of a length which allows the clinician to move about freely with scraper 124.

In use, the clinician engages compressed gas source 130 which supplies a compressed gas to cavity 128 and causes fluid pressure to build up in housing 126, forcing fluid 18 through dispenser 42. Fluid 18 contacts interface 26 of adhesive device 28 and skin 24 to which adhesive device 28 is attached to reduce the adhesion of adhesive 27 as discussed with respect to the above-described embodiments. Then, as compressed gas source 130 continues to supply compressed gas to cavity 128, scraper 124 is moved in a direction following line "P" as discussed with respect to FIG. 3 to remove adhesive device 28 from the patient. A wick 44 retains fluid 18 in scraper 124 until scraper 124 is in use. This embodiment allows the clinician to use scraper 124 without manually compressing the scraper.

Figure 12:
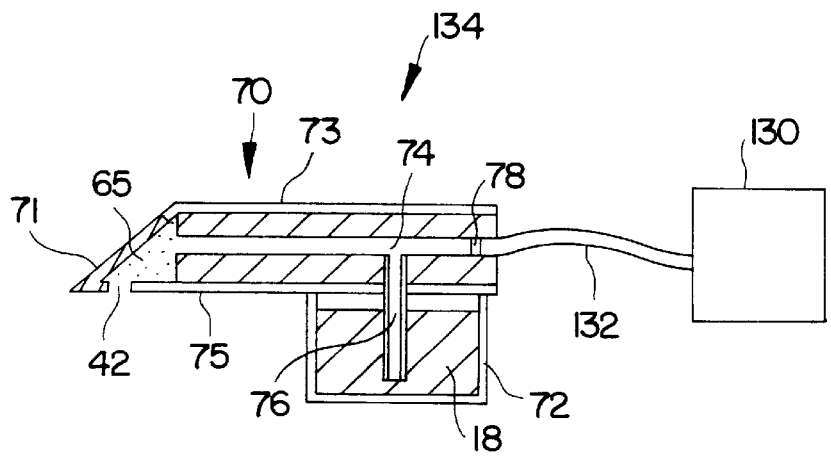
FIG. 12 is a sectional side view of an eleventh embodiment of the scraping apparatus according to the present invention.

FIG. 12 shows an eleventh embodiment of the present invention which is a variation of the seventh embodiment shown in FIG. 8. This embodiment further includes, however, an external source of a compressed gas such as an inert gas, air, or any heated or cooled gas, or the like, which will not deteriorate the adhesion characteristics of fluid 18 and is suitable for medical use. In this embodiment, scraper 134 includes a T-shaped distributor 70 having a sloping wall 71, a top wall 73, a bottom wall 75, and a dispenser 42. Dispenser 42 may be a narrow slit or a plurality of holes. The T-shaped distributor 70 also has a fluid reservoir 72 in fluid communication with first annular opening 74 via second annular opening 76. First annular opening 74 has check valve 78 disposed therein. Sloping wall 71, top wall 73, bottom wall 75, and fluid reservoir 72 are assembled using an adhesive of which the adhesion will not be reduced by fluid 18. Optionally, those components may be heat sealed or may be integrally formed. Scraper 134 further includes a source of compressed gas 130 such as an inert gas or air. Compressed gas source 130 may be, for example, an air pump or an air compressor which is attached via conduit 132 to first annular opening 74. Check valve 78 allows one-way fluid flow in the direction of sloping wall 71 allowing gas to flow into annular first opening 74 when compressed gas source 130 is engaged. Check valve 78 also prevents fluid 18 from entering conduit 132 when compressed gas source 130 is disengaged.

In use, as compressed gas is supplied from compressed gas source 130, check valve 78 opens forcing the compressed gas at great speed therethrough and, by reducing the pressure (Bernoulii's equation) in first annular opening 74, the forced gas siphons and atomizes fluid 18 from fluid reservoir 72. Atomized fluid 18 exits T-shaped distributor 70 through dispenser 42 to contact interface 26 of adhesive device 28 and skin 24 to which adhesive 27 is attached as discussed with respect to the above-described embodiments.

Figure 13:
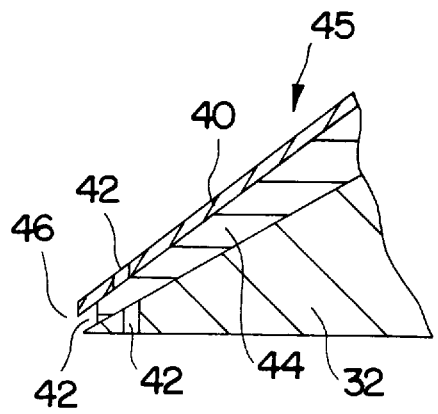
FIG. 13 is a partial section side view of the embodiment shown in FIG. 5 with more than one dispenser location.
Figure 14:
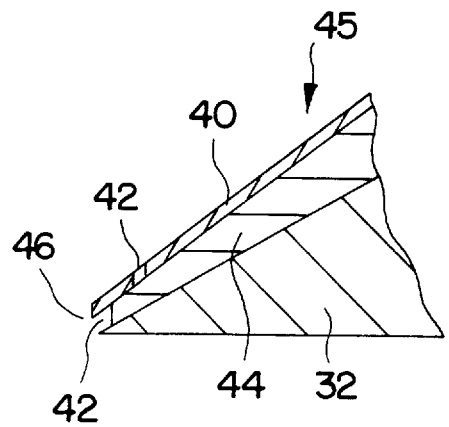
FIG. 14 is a second partial sectional side view of the embodiment shown in FIG. 5 with more than one dispenser location.
Figure 15:
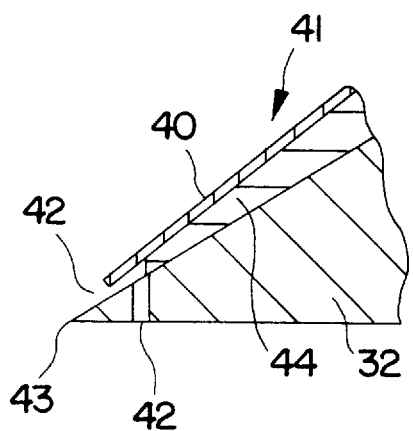
FIG. 15 is a partial sectional side view of the embodiment shown in FIG. 4B with more than one dispenser location.
Figure 16:
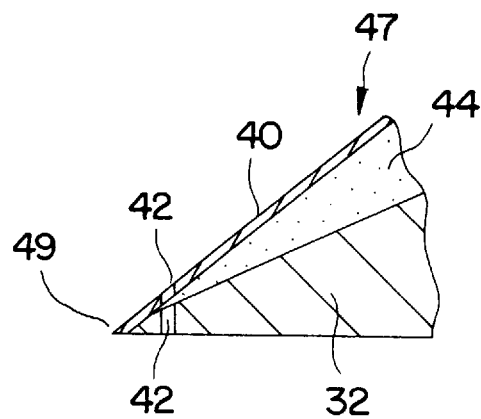
FIG. 16 is a partial sectional side view of the embodiment shown in FIG. 6A with more than one dispenser location.

In each of the above-described embodiments, dispenser 42 may be disposed in one location or more than one location in the various scrapers. For example, variations of the embodiments shown in FIGS. 4B, 5, and 6A are shown in FIGS. 13–16 with dispenser 42 in the top, bottom, and end of the scraper (as shown in FIG. 13); in the top and end of the scraper (as shown in FIG. 14); in the bottom and end of the scraper (as shown in FIG. 15); or in the top and bottom of the scraper (as shown in FIG. 16). In the configurations with more than one dispenser to dispense fluid 18, if one opening becomes blocked with adhesive or other contaminant or debris, the other opening(s) allow fluid 18 to be dispensed therethrough. In this way, an ample supply of fluid 18 is continuously dispensed at or around the portion of the scraper used for scraping the adhesive device from the skin.

The components of the above-described embodiments are formed from materials which will not be deteriorated or otherwise adversely affected by fluid 18. For example, the components of the above-described scraper embodiments, excluding wicks 44, 65, and 85; flexible sheets or membranes 34; and reservoirs 50 and 66 are formed from a thin plastic material such as polyvinyl chloride (PVC), polyethylene, polypropylene, or the like which will not be dissolved by fluid 18. Optionally, these components are formed from a thin, metallic material such as aluminum. The adhesive used to bind the various components together is selected such that the adhesion thereof is not reduced by fluid 18. For example, a hot melt adhesive is used that is not dissolved by fluid 18. Wicks 44, 65, and 85 typically are formed from an absorbent material such as a twisted, braided, or woven cotton or cotton blend, or the like. Flexible sheets or membranes 34 and reservoirs 50 and 66 are formed from, for example, a silicone rubber material, aluminum, or the like that will not be dissolved by fluid 18. Fluid 18 is any gas or liquid capable of reducing or eliminating the adhesion of adhesive 27 on adhesive device 28.

Fluid 18 may be a liquid or gas solvent or solvent-like material; a heated or cooled liquid or gas; or the like. A solvent or solvent-like material as used herein is any gas or liquid that will reduce or eliminate the adhesion of adhesive 27. For example, the liquid solvent or solvent-like material is an alcohol such as propyl alcohol, isopropyl alcohol (rubbing alcohol), or the like. In addition, a gaseous solvent or solvent-like material may be used. The heated or cooled liquid or gas is, for example, an inert gas, an inert liquid, air or water. Fluid 18 may further include a small amount of an oil or detergent so that fluid 18 may be used on patients with particularly sensitive skin.

The width of the above described scrapers is somewhat larger than the adhesive device to be removed. For example, the scraper is preferably approximately one-quarter to one-half inch wider than the width of the adhesive device to be removed.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A scraping apparatus for contacting an adhesive device and skin to which the adhesive device is attached, at an interface between the adhesive device and the skin, to remove the adhesive device from the skin, said apparatus comprising:

fluid;
   means for holding said fluid, said fluid holding means having a semi-rigid, non-elastic housing surrounding a cavity;
   semi-rigid, non-elastic pointed means for scraping the adhesive device from the skin, said scraping means having a top, a bottom and an end, and connected to and in fluid communication with said fluid holding means and having at least one first opening distal to said fluid holding means; and
   means for closing said first opening.

2. The scraping apparatus according to claim 1, wherein said fluid is a solvent.

3. The scraping apparatus according to claim 2, wherein said solvent is alcohol.

4. The scraping apparatus according to claim 3, wherein said alcohol is selected from the group consisting of propyl alcohol and isopropyl alcohol.

5. The scraping apparatus according to claim 2, wherein said solvent is heated.

6. The scraping apparatus according to claim 2, wherein said solvent is cooled.

7. The scraping apparatus according to claim 1 wherein said fluid is selected from the group consisting of a heated liquid, heated gas, cooled liquid, and cooled gas.

8. The scraping apparatus according to claim 7, wherein said fluid is selected from the group consisting of heated and cooled inert gas, inert liquid, air and water.

9. The scraping apparatus according to claim 1, wherein said fluid holding means has means for introducing said fluid into said holding means and said apparatus further comprises means for sealing said introducing means proximate said introducing means.

10. The scraping apparatus according to claim 9, wherein said introducing means is an annular hole and said sealing means is selected from the group consisting of a cylindrical plug, a cap, a clamp, a pincher, an adhesive, and heat sealing.

11. The scraping apparatus according to claim 1, wherein said fluid holding means has an open top and a flexible sheet covering said open top.

12. The scraping apparatus according to claim 1, wherein the cavity surrounded by said semi-rigid, non-elastic housing is disposed between a first member and a second member, said first member having a beveled edge and a cut out into which said housing is inserted.

13. The scraping apparatus according to claim 12, wherein said scraping means is said beveled edge of said first member and said first opening is adjacent said beveled edge and in fluid communication with said fluid holding means.

14. The scraping apparatus according to claim 1 further comprising a flexible membrane, said housing having a V-shaped cross-section and a tip and surrounding said flexible membrane.

15. The scraping apparatus according to claim 14, wherein said scraping means is said tip of said housing.

16. The scraping apparatus according to claim 1, wherein said scraping means is a tapered end of said fluid holding means having two opposing faces.

17. The scraping apparatus according to claim 16, wherein said first opening closing means is said opposing faces biased against one another.

18. The scraping apparatus according to claim 1, wherein said scraping means is a wedge-shaped member.

19. The scraping apparatus according to claim 1, wherein said scraping means is a T-shaped member having a wedge-shaped end.

20. The scraping apparatus according to claim 1, wherein said fluid holding means has an edge and said scraping means is said edge of said fluid holding means.

21. The scraping apparatus according to claim 1, wherein said means for closing said first opening is disposed inside said scraping means.

22. The scraping apparatus according to claim 1, wherein said first opening is selected from the group consisting of a slit, a groove, a slot, a hole, and a plurality of slits, grooves, slots, and holes and said means for closing said first opening is a wick.

23. The scraping apparatus according to claim 1, wherein said first opening is in said top of said scraping means.

24. The scraping apparatus according to claim 1, wherein said first opening is in said bottom of said scraping means.

25. The scraping apparatus according to claim 1, wherein said first opening is in said end of said scraping means.

26. The scraping apparatus according to claim 1, wherein said scraping means has two said first openings and one said first opening is in said top and another said first opening is in said bottom.

27. The scraping apparatus according to claim 1, wherein said scraping means has two said first openings and one said first opening is in said top and another said first opening is in said end.

28. The scraping apparatus according to claim 1, wherein said scraping means has two said first openings and one said first opening is in said bottom and another said first opening is in said end.

29. The scraping apparatus according to claim 1, wherein said scraping means has three said first openings, and one said first opening is in said top, another said first opening is in said bottom, and another said first opening is in said end of said scraping means.

30. The scraping apparatus according to claim 1, further comprising a means for propelling said fluid to said first opening.

31. The scraping apparatus according to claim 30, wherein said propelling means is a compressed gas.

32. The scraping apparatus according to claim 31, wherein said compressed gas is selected from the group consisting of inert gas, air, heated inert gas, cooled inert gas, heated air and cooled air.

33. The scraping apparatus according to claim 31, wherein said fluid holding means is adjacent said scraping means;

said compressed gas atomizes said fluid, and said compressed gas is adjacent to and in fluid communication with said fluid holding means and said scraping means; and said scraping apparatus further comprises means for preventing said fluid from entering said propelling means, and said preventing means is connected to and in fluid communication with said propelling means.

34. The scraping apparatus according to claim 33, wherein said preventing means is a first check valve.

35. The scraping apparatus according to claim 33, wherein said compressed gas is supplied from an apparatus selected from the group consisting of a flexible reservoir having a third opening in fluid communication with ambient air and a check valve disposed in said third opening; an air pump; and an air compressor.

36. The scraping apparatus according to claim 33, wherein said scraping means is a wedge-shaped member and said means for closing said first opening is disposed inside said scraping means.

37. The scraping apparatus according to claim 36, wherein said first opening is at least one slit and said means for closing said first opening is a wick.

38. The scraping apparatus according to claim 30, wherein said propelling means is gravity.

39. A scraping apparatus for contacting an adhesive device and skin to which the adhesive device is attached, at an interface between the adhesive device and the skin, said apparatus comprising:

solvent;

means for holding said solvent;

means for scraping the adhesive device from the skin, said scraping means connected to and in fluid communication with said solvent holding means and having at least one first opening distal to said solvent holding means;

means for propelling said solvent, said propelling means adjacent to and in fluid communication with said solvent holding means and said scraping means; and means for preventing said solvent from entering said propelling means, said preventing means connected to and in fluid communication with said propelling means.

40. The scraping apparatus according the claim 39, wherein said means for holding said solvent is a housing surrounding a cavity;

said scraping means is a wedge-shaped member;

said first opening is a slit;

said propelling means is selected from the group consisting of a flexible, ball-shaped reservoir having a third opening in fluid communication with the ambient air and a first check valve disposed in said third opening; an air pump; and an air compressor; and said preventing means is a second check valve.

* * * * *

UNITED STATES PATENT AND TRADE MARK OFFICE
CERTIFICATE OF CORRECTION

PATENT NO.    : 5,803,639
DATED         : September 8, 1998
INVENTOR(S)   : Gusakov et al.

It is certified that error appears in the above-identified patent and that said Letters Patent is hereby corrected as shown below:

On the title page, item: [56], under "U.S. Patent Documents", delete reference number "1,861,790", and insert therefor --1,860,790--.

Signed and Sealed this

Twentieth Day of April, 1999

Attest:

Q. TODD DICKINSON

Attesting Officer

Acting Commissioner of Patents and Trademarks